United States Patent [19]

Uchida et al.

[11] Patent Number: 4,471,648

[45] Date of Patent: Sep. 18, 1984

[54] TEMPERATURE CONTROL SYSTEM

[75] Inventors: Masaaki Uchida; Shigeo Isitani; Kohki Sone, all of Yokosuka, Japan

[73] Assignee: Nissan Motor Company, Yokohama, Japan

[21] Appl. No.: 386,356

[22] Filed: Jun. 8, 1982

[30] Foreign Application Priority Data

Jun. 11, 1981 [JP] Japan ................................ 56-88799

[51] Int. Cl.³ .......................................... G01N 27/26
[52] U.S. Cl. ...................................... 73/23; 204/408; 123/440
[58] Field of Search ................. 73/23, 27 R; 204/406, 204/407, 408, 424, 431; 123/440, 489

[56] References Cited

U.S. PATENT DOCUMENTS

| 4,332,225 | 6/1982 | Cox et al. | 204/424 |
| 4,359,030 | 11/1982 | Sone et al. | 204/406 |
| 4,365,604 | 12/1982 | Sone | 123/440 |

FOREIGN PATENT DOCUMENTS

| 1512 | 4/1979 | European Pat. Off. |
| 9129 | 4/1980 | European Pat. Off. |
| 1603599 | 6/1971 | France |
| 2126039 | 9/1972 | France |
| 2393363 | 2/1978 | France |
| 2015175 | 9/1979 | United Kingdom |

OTHER PUBLICATIONS

Journal of Physics E, vol. 10, No. 9, Sep. 1977, pp. 881-883 by Beigang et al., "A Reliable, Low-Cost, Temperature-Controlled Oven".

Primary Examiner—Stephen A. Kreitman
Attorney, Agent, or Firm—Schwartz, Jeffery, Schwaab, Mack, Blumenthal & Koch

[57] ABSTRACT

A temperature control system is disclosed wherein a heater of a gas sensor and a plurality of reference resistors cooperate to form a bridge circuit. The temperature control system comprises a comparator means for monitoring a balancing voltage of the bridge circuit and generating a control signal indicative of the balancing voltage and an electric power amplifier means responsive to the control signal for varying a voltage applied to the bridge circuit in such a manner to reduce the balancing voltage. The gas sensor has mounted therein at least one of the plurality of reference resistors, which reference resistor having a resistance resulting from multiplying the resistance of the heater with a constant.

4 Claims, 4 Drawing Figures

TEMPERATURE CONTROL SYSTEM

BACKGROUND OF THE INVENTION

1. Field of the Invention

The present invention relates to a temperature control system which controls the temperature of a heater mounted in a gas sensor in such a manner as to keep the heater at a substantially constant temperature.

2. Description of the Prior Art

A known gas sensor is provided with a heater for heating a gas concentration measuring part to a suitable temperature at which the gas concentration measuring part functions efficiently and accurately. To control the temperature of the heater, it has been tried to sense the actual temperature of the heater with a temperature sensing element. The temperature sensed by the sensing element is compared with a predetermined temperature at a comparator. The control is carried out such that when the sensed temperature is lower than the predetermined temperature, a relay switch is closed to connect a source of electric power to the heater, while, when the sensed temperature is higher than the predetermined temperature the relay is opened to disconnect the heater from the source of electric power. The temperature sensing element is embedded in a base plate wherein the heater is disposed. However, it has been found difficult to embed the temperature sensing element in the base plate.

SUMMARY OF THE INVENTION

An object of the present invention is to provide a temperature control system which does not use a temperature sensing element.

According to the present invention, there is provided a temperature control system which comprises a heater, a plurality of reference resistors cooperating with the heater to form a bridge circuit, means for monitoring a balancing voltage of the bridge circuit and means for varying a voltage applied to the bridge circuit in such a manner as to reduce the balancing voltage.

For increasing interchangeability of gas sensors, the gas sensor has mounted therein at least one of the plurality of reference resistors which form the bridge circuit. That reference resistor which is mounted in the gas sensor should have a resistance resulting from multiplying the resistance of the heater with a constant.

Accordingly, a specific object of the present invention is to provide a temperature control system wherein replacement of an old gas sensor with a new one is quite easy.

BRIEF DESCRIPTION OF THE DRAWINGS

The present invention is specifically described hereinafter in connection with the accompanying drawings, wherein.

DETAILED DESCRIPTION OF THE INVENTION

Figure 1:
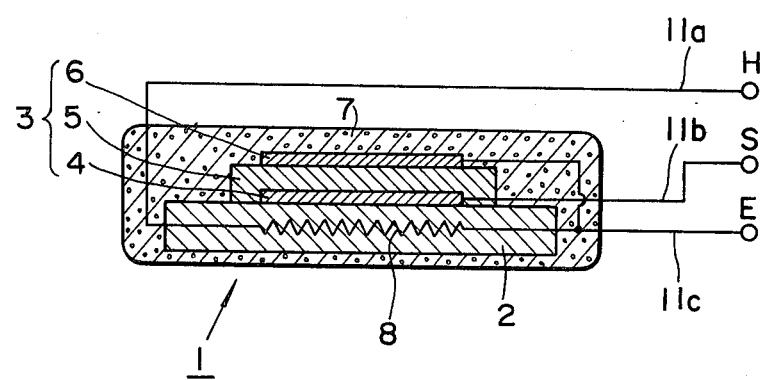
FIG. 1 is a schematic sectional view of an oxygen concentration measuring element illustrating a typical structure of the oxygen concentration measuring element.
Figure 2:
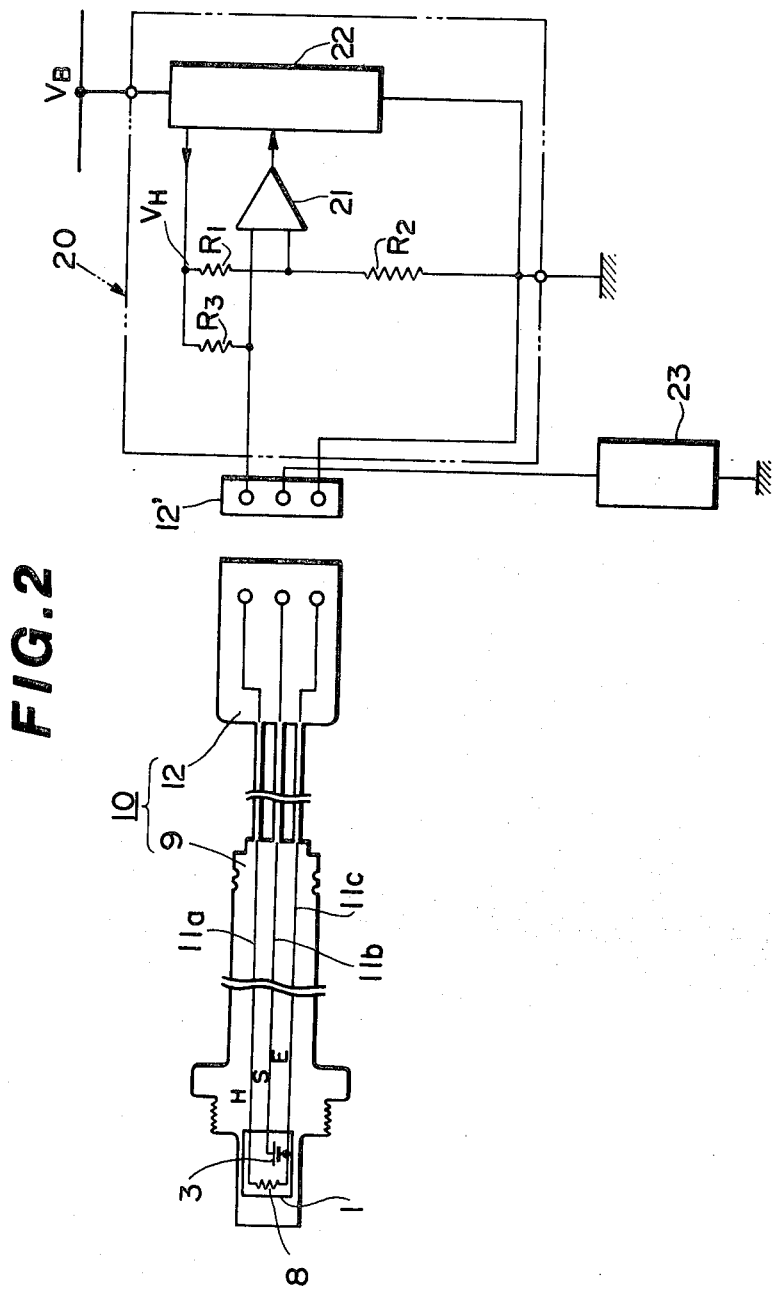
FIG. 2 is a block and wiring diagram of a first embodiment of a temperature control system according to the present invention.

Referring to FIGS. 1 and 2, a temperature control system comprises an oxygen concentration measuring element 1 utilizing the principle of oxygen concentration cell.

As shown in FIG. 1, the oxygen concentration measuring element 1 comprises a base plate 2, an oxygen concentration measuring part 3 that includes a laminate of a reference electrode layer 4, an oxygen ion conductive solid electrolyte layer 5 and a measuring electrode layer 6 arranged one after another in this order. A porous protecting layer 7 covers the whole outer surfaces of the measuring part. Since the oxygen ion conductive solid electrolyte layer 5 exhibits the best electromotive force characteristic at a temperature ranging from about 600° to 700° C., a heater 8 is embedded in the base plate 2 to controllably keep the oxygen concentration measuring part 3 at a preset temperature falling in said temperature range. Although in the illustrated example the oxygen ion conductive solid electrolyte layer 5 is in the form of a layer, it may take the form of a tubular shape or a pot shape.

As shown in FIG. 2, this oxygen concentration measuring element 1 is attached to a holder 9 and has its lead lines 11a, 11b and 11c connected with a connector 12, thus forming a gas sensor, viz., an oxygen sensor 10.

Referring to FIG. 2, indicated by 20 is a temperature control circuit wherein one end of the heater 8 is connected via a lead line 11 and a connector 12' to one terminal of a comparator 21 and via a resistor $R_3$ to an output side of an electric power amplifier 22, the output side of the electric power amplifier 22 is connected to the input terminal of the comparator 21 via a resistor $R_1$, and the other input terminal of the comparator 21 is grounded via a resistor $R_2$. The other side of the heater 8 is grounded via a lead line 11c and connectors 12, 12'. That is, the heater 8 (resistor $R_H$) cooperates with the reference resistors $R_1$, $R_2$ and $R_3$ to form a bridge circuit wherein the comparator 21 detects the balancing voltage of the above mentioned bridge circuit and feeds its output to the electric power amplifier 22 to control an output voltage $V_H$ of the electric power amplifier 22 to maintain the temperature of the heater 8 at a substantially predetermined temperature. Indicated by 23 is an oxygen concentration measuring circuit connected to the oxygen concentration measuring element 3 wherein oxygen concentration within the atmosphere is measured by allowing a control current to flow between the reference electrode 4 of the oxygen concentration measuring element 1 and the measuring electrode 6 so as to keep a voltage related to the partial pressure of oxygen substantially constant, and measuring an output voltage of the oxygen concentration measuring element 1.

Explaining further the temperature control of said heater 8, if we assume an electric voltage on one of the input terminals of the comparator 21 as $e_1$ and an electric voltage on the other input terminal as $e_2$, we can express $$e_1 = V_H \cdot R_H / (R_3 + R_H)$$

$$e_2 = V_H \cdot R_2 / (R_1 + R_2)$$

and in the event that the resistance of the resistor $R_H$ of the heater is smaller than a predetermined value (that is, in the event that it is judged the temperature of the heater 8 is lower than a predetermined temperature), since $e_1<e_2$, the output electric voltage $V_H$ of the electric power amplifier is increased to increase the temperature of the heater 8, thus increasing the resistance of the resistor $R_H$ of the heater 8 until $e_1=e_2$ is satisfied. In the event that the resistance of the resistor $R_H$ of the heater 8 is greater than the predetermined value (that is, in the event that the temperature of the heater 8 is higher than the predetermined temperature), since $e_1>e_2$, the output electric voltage $V_H$ is decreased to decrease the temperature of the heater 8, thus decreasing the resistance of the resistor $R_H$ until $e_1=e_2$ is satisfied.

Figure 3:
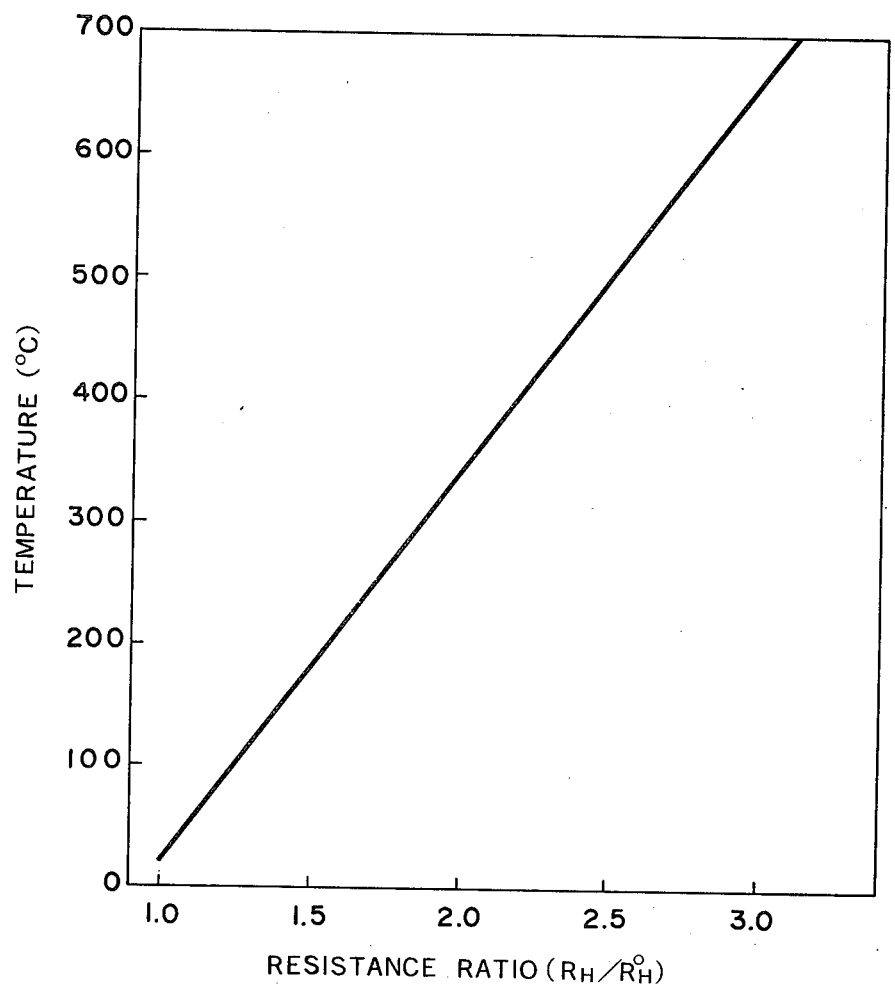
FIG. 3 is a graph illustrating temperature vs., resistance ratio.
Figure 4:
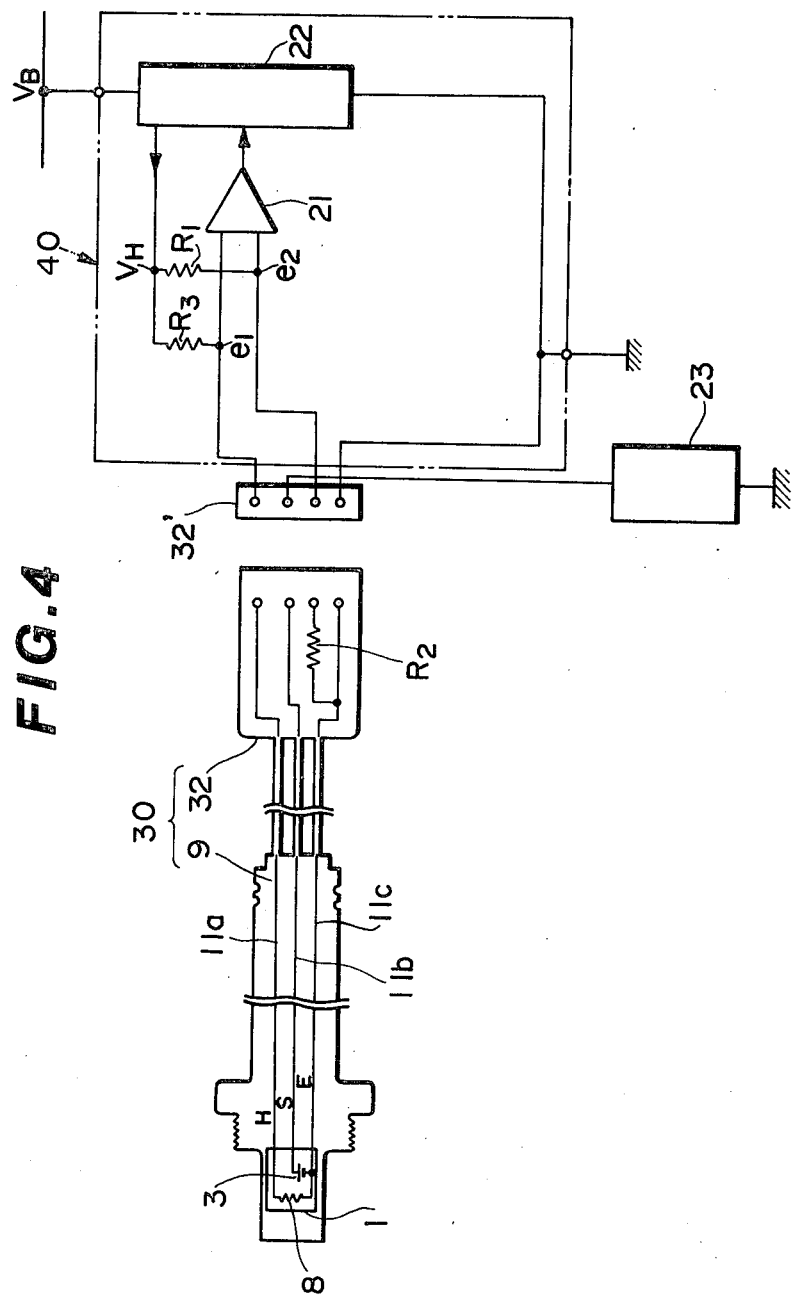
FIG. 4 is a block and wiring diagram of a second embodiment of a temperature control system according to the present invention.

Referring to FIGS. 3 and 4, a second embodiment is explained which has solved a problem encountered in the embodiment just described in connection with FIGS. 1 and 2.

In the case of the first embodiment, even if the resistance of the resistor $R_H$ of the heater 8 is controlled to satisfy the relationship $R_H=R_2 \cdot R_3/R_1$, viz., even if the resistance of the resistor $R_H$ of the heater 8 is controllably maintained constant, the temperature of the heater 8 varies as shown in FIG. 3 with variation in the resistance $R_H°$ of the heater 8 at a room temperature (20° C.). Thus, in the event that the resistances of the respective heaters 8 vary from one to another, the temperatures of the respective heaters 8 vary accordingly even if the control is carried out to satisfy $e_1=e_2$. Because, it is the conventional practice to select reference resistors $R_1$, $R_2$ and $R_3$ for respective heaters to cause the respective heaters 8 to produce a predetermined temperature, a problem has arisen in replacing in old oxygen sensor with a new oxygen sensor that unless a heater of a new oxygen sensor having the same resistance at the room temperature as that of the heater 8 of the old oxygen sensor 10 is selected or the resistances of the reference resistors of the temperature control circuit 20 are varied in correspondence with a new resistance at the room temperature of the heater of the new oxygen sensor 10, it has been impossible to effect the temperature control with the new oxygen sensor to provide the same result in temperature as being obtained with the use of the old oxygen sensor. In manufacturing oxygen sensors, it is very difficult to manufacture heaters 8 with the same resistance and it is not acceptable to select the oxygen sensors with heaters having the same resistance because it leads to a bad yield. Further, it is not practical to replace reference resistors of the temperature control circuit 20. Thus, in the case there is adopted a management system wherein the oxygen sensors 10 are stocked in respective service works in various areas for replacement, it is necessary to stock oxygen sensors having a numerous different kinds of resistances $R_H°$ in each service work for carrying out replacement with good precision, thus leading to a bad interchangeability of the oxygen sensors.

This embodiment is based upon the recognition that there exists a characteristic that at any given temperature, $R_H=CR_H°$ (C=constant), which holds despite any variations in $R_H°$.

Explaining the second embodiment in detail in connection with FIG. 4, this embodiment is different from the first embodiment in that an oxygen sensor has mounted in a connector 32 thereof a reference resistor $R_2$ forming part of a bridge circuit. An oxygen concentration measuring element 1 has lead lines 11a, 11b and 11c connected to the connector 32. The resistor $R_2$ mounted in the connector 32 has one end connected to the lead line 11c and is adapted to be grounded or connected to the earth. Referring to the temperature control circuit 40, one of two input terminals of a comparator 21 is connected to one end of the heater 8 via the lead line 11a and connectors 32, 32' and also connected to an output side of an electric power amplifier 22 via a resistance $R_3$, and the output side of the electric power amplifier 22 is connected to the other input terminal of the comparator 21 via a resistor $R_1$, and the other input terminal of the comparator 21 is connectable to the ground via the connectors 32, 32' and the resistor $R_2$. As a result, when the connector 32 of the oxygen sensor 30 is connected to the connector 32' of the temperature control circuit 40, the heater 8 (resistor $R_H$) and reference resistor $R_2$ of the oxygen sensor 30 cooperate with the reference resistors $R_1$ and $R_3$ of the temperature control circuit 40 to form the bridge circuit. The comparator 21 detects the balancing voltage of the bridge circuit and feeds it as an output to the electric power amplifier 22 so as to control the output voltage $V_H$ of the electric power amplifier 22 to keep the resistance of the resistor $R_H$ (temperature) of the heater substantially constant. Indicated by 23 is an oxygen concentration measuring circuit connected to the oxygen concentration measuring element 3 via the lead lines 11b, 11c and the connectors 32 and 32', which measuring circuit allows a reference current to flow between the reference electrode 4 and measuring electrode 6 of the oxygen concentration measuring element 3 so as to keep a voltage related to the partial pressure of oxygen substantially constant and measures an output voltage of the oxygen concentration measuring element 3, thus detecting the oxygen concentration in the atmosphere.

According to the characteristic of the bridge circuit, a relationship $R_2/R_H=R_1/R_3$ holds at a predetermined temperature and since as shown in FIG. 3 there is a relationship that $R_H=CR_H°$, $R_2=(R_1/R_3)\cdot R_H=C\cdot(R_1/R_3)\cdot R_H°$ holds, and thus as the reference resistor $R_2$ which is to be mounted to the above-mentioned oxygen sensor 30, a resistor having a resistance resulting from multiplying a resistance $R_H°$ at room temperature of the heater 8 with a constant ($K=C\cdot R_1/R_3$) should be chosen. If setting is made that $R_2=K\cdot R_H°$, the resistor $R_H$ of the heater 8 is controlled to satisfy $R_H=K\cdot R_H° \, (R_3/R_1)$ by means of the above-mentioned control circuit 40, so that $R_H/R_H°=K(R_3/R_1)$ holds. The fact that $R_H/R_H°$ is constant allows the heater to produce a predetermined temperature as shown in FIG. 3. Accordingly, in manufacturing the oxygen sensors 30, the resistance $R_H°$ at room temperature of the heater 8 is measured and a resistor having a resistance $R_2=K\cdot R_H°$ is used as a reference resistor to be accommodated in the connector 32; and what is only necessary is to let each of service works in various districts store such oxygen sensors as manufactured in the above manner as repair parts. Accordingly, the replacement of an old oxygen sensor with a new one can be effected at each service work without due regard to the variation in the resistance of the heater of the oxygen sensor 30 and without due adjustment of the reference resistors $R_1$ and $R_3$ of the temperature control circuit 40.

Referring to the bridge circuit, because there is a relationship $R_H=R_2 \cdot R_3/R_1$, a desired one of reference resistors $R_1$, $R_2$ and $R_3$ may be accommodated in the oxygen sensor 30. In mounting the reference resistors $R_2$ and $R_3$ on the oxygen sensor 30, the resistors with small resistances are chosen as the reference resistors $R_2$ and $R_3$ when the resistance $R_H°$ of the heater 8 at room temperature is lower than a predetermined value. In mounting the reference resistor $R_1$ on the oxygen sensor 30, the situation is quite the opposite to the case mentioned above. However, as shown in the embodiment shown in FIG. 4, it is preferrable to use the reference resistor $R_2$ as the reference resistor to be mounted on the oxygen sensor 30 for the merit that a the amount of current it must withstand is small and a common earth may be used.

In this embodiment, there has been shown an example that the reference resistor $R_2$ is mounted on the connector 32, the reference resistor may be mounted on the holder or lead line, if desired. In any event the reference resistor should be mounted within an area where the heat has little influence.

Although in the above embodiments, the invention is applied to an oxygen concentration measuring element, it may be applied to any gas sensor where temperature control is desired.

What is claimed is:

1. An apparatus comprising:

a gas sensor having a heater;

a bridge circuit comprising a plurality of reference resistors, at least one of said plurality of reference resistors being mounted within said gas sensor;

a source of electric power applying a voltage to said bridge circuit;

means for monitoring a balancing voltage of said bridge circuit and generating a control signal indicative of said balancing voltage; and means responsive to said control signal for varying said voltage applied to said bridge circuit in such a manner as to reduce said balancing voltage.

2. An apparatus as claimed in claim 1, wherein said at least one of said plurality of reference resistors has a resistance resulting from multiplying a resistance of said heater with a constant.

3. An apparatus as claimed in claim 2, wherein said constant is expressed by $K=C \cdot (R_1/R_3)$.

4. An apparatus as claimed in claim 2, 3, or 1, wherein said gas sensor comprises an element holder, a gas concentration measuring element supported by said element holder, and a connector carrying terminals electrically connected via respective lead lines with said gas concentration measuring element.

* * * * *